(12) United States Patent
Smigel et al.

(10) Patent No.: US 9,452,128 B2
(45) Date of Patent: *Sep. 27, 2016

(54) LIP BALM

(71) Applicant: Robell Research, New York, NY (US)

(72) Inventors: Lucia Smigel, New York, NY (US); Tammy Ha, Reseda, CA (US)

(73) Assignee: Robell Research, Inc., New York, NY (US)

( * ) Notice: Subject to any disclaimer, the term of this patent is extended or adjusted under 35 U.S.C. 154(b) by 223 days.

This patent is subject to a terminal disclaimer.

(21) Appl. No.: 13/911,176

(22) Filed: Jun. 6, 2013

(65) Prior Publication Data

US 2013/0330289 A1     Dec. 12, 2013

Related U.S. Application Data

(60) Provisional application No. 61/656,131, filed on Jun. 6, 2012.

(51) Int. Cl.
| | | |
|---|---|---|
| *A61K 8/97* | (2006.01) | |
| *A61K 8/19* | (2006.01) | |
| *A61K 8/92* | (2006.01) | |
| *A61K 8/68* | (2006.01) | |
| *A61K 8/73* | (2006.01) | |
| *A61K 8/65* | (2006.01) | |
| *A61K 8/26* | (2006.01) | |
| *A61Q 19/00* | (2006.01) | |

(52) U.S. Cl.
CPC . *A61K 8/97* (2013.01); *A61K 8/19* (2013.01); *A61K 8/26* (2013.01); *A61K 8/65* (2013.01); *A61K 8/68* (2013.01); *A61K 8/735* (2013.01); *A61K 8/92* (2013.01); *A61K 8/922* (2013.01); *A61K 8/927* (2013.01); *A61Q 19/001* (2013.01)

(58) Field of Classification Search
None
See application file for complete search history.

(56) References Cited

U.S. PATENT DOCUMENTS

| 5,395,620 | A | 3/1995 | Huc et al. |
|---|---|---|---|
| 5,420,248 | A | 5/1995 | Devictor et al. |
| 5,476,671 | A | 12/1995 | Cho et al. |
| 5,622,656 | A | 4/1997 | Huc et al. |
| 6,660,281 | B1 | 12/2003 | Nakanishi et al. |
| 2010/0286102 | A1 | 11/2010 | Vielhaber |
| 2012/0189684 | A1 | 7/2012 | Buckley et al. |

OTHER PUBLICATIONS

Boswellic Acid, Wikipedia: http://en.wikipedia.org/wiki/Boswellic_acid (accessed Mar. 19, 2013).
Hirulip Product information from Lipotec; Jun. 2010 (9 pages).
Marine Filli9ng Spheres Product Information from BASF (7 pages) (Mar. 2008).
Volulip product information from Sederma (2009).
MSDS for Dow Corning 2503 Cosmetic Wax (9 page) (Feb. 14, 2009).
Ceramides; Chemistry, Occurence, Biology and Analysis; The AOGS Lipid Library, http://lipidlibrary.aocs.org/lipids/ceramide/index.htm (7 pages) updated Feb. 7, 2013.
Lintner et al; The effect of a synthetic ceramide-2 on transepidermal water loss after stripping of sodium lauryl sulfate treatment: an in vivo study; International Journal of Cosmetic Science 19, 15-25 (1997).

*Primary Examiner* — Abigail Fisher
*Assistant Examiner* — Frank Choi
(74) *Attorney, Agent, or Firm* — Grace J. Fishel

(57) ABSTRACT

A lip balm for protecting and rehydrating lips is disclosed containing a synthetic ceramide, an anti-irritant compound, sodium hyaluronate, a cosmetic wax, boswellian oil, extract of the *Portulaca pilosa* plant, a peptide, dehydrated microspheres of marine collagen and glycosaminoglycans, and mica.

3 Claims, No Drawings

9,452,128 B2

LIP BALM

This application claims priority of U.S. Provisional Patent Application Ser. No. 61/656,131, filed Jun. 6, 2012.

FIELD OF INVENTION

Lips are the most susceptible to dryness and cracking of any part of the skin. Topical lip balm products such as the present invention protect and help restore lips from the effect of dryness and cracking.

BACKGROUND OF THE INVENTION

Lips are continuously moving and subjected to repeated stress (ultraviolet radiation, dry air, etc.). The lip area is fragile by nature and needs protection in order to overcome the deficiency, or gradual decline of dermal macromolecules. Naturally dry through the fineness of the barrier and absence of moisturizing and lipid restoring glands, the vermilion of the lips is continuously subjected to drying. The mechanisms resulting in moisturization have to be strengthened to limit chapping and cracking. The vermilion of the lips is devoid of sebaceous and sweats glands. Unlike the skin, the lips have no hydrolipid protective film.

Aging of the lip zone is characterized by increased water loss, loss of volume and changes in syntheses which gives rise to a decrease in dermal density. The progressive reduction in collagens accompanied by the fall in collagen I and collagen III levels is largely responsible for the gradual loss of dermal thickness and hence the decrease in lip volume.

SUMMARY OF THE INVENTION

This invention is an improved lip balm product, comprising hyaluronic acid, sodium hyaluronate, *Portulaca* extract, boswellic acids, cosmetic wax, honeysuckle, shea butter, and fragrance.

DETAILED DESCRIPTION OF THE PREFERRED EMBODIMENT

The invention preferably consists of the active ingredients marine atelocollagen, marine chrondroitin sulfate, glycosaminoglycans, a synthetic ceramide, anti-irritant, sodium hyaluronate, extract of the *Portulaca pilosa* plant and a matrikin-mimetic peptide. The active ingredients are provided in a base medium of oils and waxes, with fragrances and moisturizers added to provide a more consumer-friendly product. Table 1 sets out a preferred listing of active ingredients, and Table 2 sets out a preferred listing of the inactive ingredients.

TABLE 1

Active Ingredients synthetic ceramide and anti-irritant compounds between 0.5 and 3.5%
sodium hyaluronate between 0.5 and 3%
cosmetic wax 2503 between 5 and 12%
boswellian oil between 0.2 and 1%
extract of the *Portulaca pilosa* plant with a peptide between 0.5 and 3%
dehydrated microspheres of marine collagen and glycosaminoglycans between 1.5 and 5.5%
mica (light diffusing powder) between 1 and 6.5%

TABLE 2

Inactive Ingredients sweet almond oil between 10 and 20%
castor oil between 10 and 20%
beeswax between 5 and 12%
paraffin wax between 5 and 12%
cetyl palmitate between 3 and 7%
cetearyl alcohol between 3 and 7%
candelilla wax between 0.5 and 1.2%
ozokerite between 2 and 4%
stearic acid between 0.2 and 1%
alphabisabolol between 0.1 and 0.3%
shea butter between 0.2 and 1%
C12-15 alkyl benzoate between 4 and 8%
tridecyl trimellitate between 2 and 6%
cetyl alcohol between 1 and 5%
petrolatum between 1 and 3%
fragrance between 0.4 and 1.2%
Honey suckle between 0.02 and 0.2%

A component of the invented lip balm product is dehydrated microspheres of marine collagen and glycosaminoglycans. These microspheres have the capacity to rehydrate in the presence of water and regain their initial volume. While dehydrated, the microspheres are small enough to penetrate crevices in lips. The microspheres increase in size through absorption of moisture in the lips, which causes a smoothing of the lip surface. The microspheres are slowly degraded by enzymes in the lip, which allows the microspheres to release the moisture initially absorbed from the lips, returning the moisture to the lips. The microspheres are preferably comprised of marine atelocollagen and marine chrondroitin sulfate, as disclosed in U.S. Pat. Nos. 5,395,620, 5,420,248 and 5,622,656, as well as non-US counterparts.

Another component of the invented lip balm product is a synthetic ceramide and anti-irritant compound. Skin tissue has a protective layer referred to as a lipid bilayer, which helps bind corneocytes to protect skin tissue from external damage. The lipid bilayer is itself comprised of ceramides, fatty acids and cholesterol. Skin tissue with decreased ceramide levels have been shown to suffer a variety of damage, but unlike fatty acids and cholesterol, ceramides cannot be easily replaced. A synthetic ceramide can provide similar protection to naturally occurring ceramides. The synthetic ceramide combines synthetic ceramide with an anti-inflammatory known as alpha-Bisabolol, as well as Phytosterol and Stearic acid, to supplement the lipid bilayer of skin tissue.

A further component of the invented lip balm product are small particles of sodium hyaluronate. Skin tissue, including lip tissue, contains hyaluronic acid, a natural polymer. Hyaluronic acid maintains tissue hydration and helps retain water within the skin tissue. Sodium hyaluronate particles penetrate the lip tissue, and increase in size by absorbing moisture from the lip tissue as well as external moisture. The swelling of the sodium hyaluronate particles increase the volume of the lip tissue, reducing wrinkles and plumping the lips. Preferably, the sodium hyaluronate particles are delivered in an oil-based suspension, to prevent particle expansion before penetration into the lip tissue.

Yet another component of the invented lip balm product is a compound of an extract of the *Portulaca pilosa* plant with a peptide. The *Portulaca pilosa* plant, also known as "Kiss-Me-Quick," is part of the purslane family of edible plants." This component combines an extract of the *Portulaca pilosa* plant with a matrikin-mimetic peptide for the purposes of restoring lip volume and firmness.

While certain novel features of the present invention have been shown and described, it will be understood that various omissions, substitutions and changes in the forms and details of the device illustrated and in its operation can be made by those skilled in the art without departing from the spirit of the invention.

We claim:

1. A composition for protecting and rehydrating lips comprising:
   synthetic ceramide between 0.5 and 3.5%;
   sodium hyaluronate between 0.5 and 3%;
   cosmetic wax between 5 and 12%;
   boswellian oil between 0.2 and 1%;
   extract of the *Portulaca pilosa* plant and a peptide between 0.5 and 3%;
   dehydrated microspheres of marine collagen and glycosaminoglycans between 1.5 and 5.5%; and
   mica (light diffusing powder) between 1 and 6.5%.

2. A composition for protecting and rehydrating lips comprising:
   synthetic ceramide between 0.5 and 2.5%;
   sodium hyaluronate between 1.5 and 3%;
   cosmetic wax between 6 and 9%;
   boswellian oil between 0.4 and 0.7%;
   extract of the *Portulaca pilosa* plant and a peptide between 0.5 and 2.8%;
   dehydrated microspheres of marine collagen and glycosaminoglycans between 2 and 4%; and
   mica (light diffusing powder) between 1.5 and 4.5%.

3. The composition of claims 1 or 2 further comprising:
   sweet almond oil between 10 and 20%;
   castor oil between 10 and 20%;
   beeswax between 5 and 12%;
   paraffin wax between 5 and 12%;
   cetyl palmitate between 3 and 7%;
   cetearyl alcohol between 3 and 7%;
   candelilla wax between 0.5 and 1.2%;
   ozokerite between 2 and 4%;
   stearic acid between 0.2 and 1%;
   alphabisabolol between 0.1 and 0.3%;
   shea butter between 0.2 and 1%;
   C12-15 alkyl benzoate between 4 and 8%;
   tridecyl trimellitate between 2 and 6%;
   cetyl alcohol between 1 and 5%;
   petrolatum between 1 and 3%;
   fragrance between 0.4 and 1.2%; and
   honey suckle between 0.02 and 0.2%.

* * * * *